United States Patent
Lu et al.

(10) Patent No.: US 11,410,110 B2
(45) Date of Patent: Aug. 9, 2022

(54) ALERT GENERATION BASED ON A COGNITIVE STATE AND A PHYSICAL STATE

(71) Applicant: International Business Machines Corporation, Armonk, NY (US)

(72) Inventors: Fang Lu, Billerica, MA (US); Paul R. Bastide, Ashland, MA (US); Ishwarya Rajendrababu, Hoboken, NJ (US); SathyaNarayanan Srinivasan, Austin, TX (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 303 days.

(21) Appl. No.: 16/533,550

(22) Filed: Aug. 6, 2019

(65) Prior Publication Data
US 2021/0042680 A1    Feb. 11, 2021

(51) Int. Cl.
| | |
|---|---|
| G06Q 10/06 | (2012.01) |
| G06Q 10/10 | (2012.01) |
| G06N 5/02 | (2006.01) |
| G10L 15/183 | (2013.01) |
| G06N 20/00 | (2019.01) |
| A61B 5/00 | (2006.01) |
| G06F 1/16 | (2006.01) |
| G06F 40/20 | (2020.01) |

(52) U.S. Cl.
CPC ..... *G06Q 10/06398* (2013.01); *A61B 5/0024* (2013.01); *G06F 1/163* (2013.01); *G06F 40/20* (2020.01); *G06N 5/02* (2013.01); *G06N 20/00* (2019.01); *G10L 15/183* (2013.01); *A61B 2505/01* (2013.01)

(58) Field of Classification Search
CPC .............................. G06Q 10/06; G06Q 10/10
USPC ....................................................... 705/7.42
See application file for complete search history.

(56) References Cited

U.S. PATENT DOCUMENTS

| | | |
|---|---|---|
| 7,657,443 B2 | 2/2010 | Crass et al. |
| 8,725,254 B2 | 5/2014 | Freeman |
| 2006/0070895 A1 | 4/2006 | Khawaja |

(Continued)

OTHER PUBLICATIONS

Well, P., et al., "Effectively and Securely Using the Cloud Computing Paradigm", NIST, Oct. 7, 2009, 80 pp.

(Continued)

*Primary Examiner* — Nga B Nguyen
(74) *Attorney, Agent, or Firm* — Konrad, Raynes, Davda & Victor LLP; Janaki K. Davda

(57) ABSTRACT

Provided are techniques for alert generation based on a cognitive state and a physical state. Wearables data, text communications, voice communications, and images of a caregiver providing care to a patient are obtained. The wearables data, the text communications, the voice communications, and the images are analyzed to identify a cognitive state and a physical state of the caregiver. The cognitive state and the physical state are compared to one or more care rules associated with tasks of the caregiver for the patient. In response to the comparison indicating any one of the cognitive state and the physical state prevent the caregiver from executing the tasks, an alert is generated. One or more recommendations for resolving the alert based on one or more recommendation rules are generated.

18 Claims, 6 Drawing Sheets

(56) References Cited

U.S. PATENT DOCUMENTS

| | | | |
|---|---|---|---|
| 2013/0281798 A1 | 10/2013 | Rau et al. | |
| 2015/0099946 A1* | 4/2015 | Sahin | G16H 50/20 |
| | | | 600/301 |
| 2016/0381328 A1* | 12/2016 | Zhao | G06F 1/1694 |
| | | | 348/154 |
| 2017/0199973 A1 | 7/2017 | Walton et al. | |
| 2017/0319123 A1* | 11/2017 | Voss | A61B 5/6803 |
| 2017/0340270 A1 | 11/2017 | Ganesh | |
| 2017/0372020 A1 | 12/2017 | Govro et al. | |
| 2018/0042542 A1 | 2/2018 | Cronin et al. | |
| 2018/0060495 A1 | 3/2018 | Mahapatra et al. | |
| 2018/0211724 A1* | 7/2018 | Wang | G16H 40/20 |
| 2019/0189259 A1* | 6/2019 | Clark | G16H 70/40 |
| 2019/0198167 A1* | 6/2019 | Durlach | A61B 5/0077 |
| 2019/0209022 A1* | 7/2019 | Sobol | A61B 5/0002 |
| 2019/0296987 A1* | 9/2019 | Cotton | G16H 80/00 |
| 2020/0137357 A1* | 4/2020 | Kapoustin | G06K 9/6292 |
| 2020/0279315 A1* | 9/2020 | Manggala | G06F 16/285 |
| 2021/0027759 A1* | 1/2021 | Ogawa | G10L 15/28 |
| 2021/0027878 A1* | 1/2021 | He | G16H 40/20 |

OTHER PUBLICATIONS

Well, P., et al., "The NIST Definition of Cloud Computing", NIST, Special Publication 800-145, Sep. 2011, 7 pp.

Pooyania, S., et al., "Examining the Relationship Between Family Caregivers' Emotional States and Ability to Empathize with Patients with Multiple Sclerosis", International Journal of MS Care, 18(3), [online] May-Jun. 2016, [Retrieved on Mar. 25, 2019], Retrieved from the Internet at <URL: https://www.ncbi.nlm.nih.gov/pmc/articles/PMC4886998/>, 14 pp.

\* cited by examiner

ALERT GENERATION BASED ON A COGNITIVE STATE AND A PHYSICAL STATE

BACKGROUND

1. Field of the Invention

Embodiments of the invention relate to alert generation based on a cognitive state and a physical state. In particular, embodiments of the invention relate to generating alerts for caregivers.

2. Description of the Related Art

Caregivers often experience stress (e.g., due to physical work and dealing with difficult patients). The caregivers and care providers may be going through a difficult time due to various factors, such as have their own health conditions, family burdens, and other issues. All of this may lead to emotional and physical stress that negatively impacts care of the patient.

SUMMARY

In accordance with embodiments, a computer-implemented method is provided for alert generation based on a cognitive state and a physical state. The computer-implemented method comprises operations. Wearables data, text communications, voice communications, and images of a caregiver providing care to a patient are obtained. The wearables data, the text communications, the voice communications, and the images are analyzed to identify a cognitive state and a physical state of the caregiver. The cognitive state and the physical state are compared to one or more care rules associated with tasks of the caregiver for the patient. In response to the comparison indicating any one of the cognitive state and the physical state prevent the caregiver from executing the tasks, an alert is generated. One or more recommendations for resolving the alert based on one or more recommendation rules are generated.

In accordance with other embodiments, a computer program product is provided for alert generation based on a cognitive state and a physical state. The computer program product comprises a computer readable storage medium having program code embodied therewith, the program code executable by at least one processor to perform operations. Wearables data, text communications, voice communications, and images of a caregiver providing care to a patient are obtained. The wearables data, the text communications, the voice communications, and the images are analyzed to identify a cognitive state and a physical state of the caregiver. The cognitive state and the physical state are compared to one or more care rules associated with tasks of the caregiver for the patient. In response to the comparison indicating any one of the cognitive state and the physical state prevent the caregiver from executing the tasks, an alert is generated. One or more recommendations for resolving the alert based on one or more recommendation rules are generated.

In yet other embodiments, a computer system is provided alert generation based on a cognitive state and a physical state. The computer system comprises one or more processors, one or more computer-readable memories and one or more computer-readable, tangible storage devices; and program instructions, stored on at least one of the one or more computer-readable, tangible storage devices for execution by at least one of the one or more processors via at least one of the one or more memories, to perform operations. Wearables data, text communications, voice communications, and images of a caregiver providing care to a patient are obtained. The wearables data, the text communications, the voice communications, and the images are analyzed to identify a cognitive state and a physical state of the caregiver. The cognitive state and the physical state are compared to one or more care rules associated with tasks of the caregiver for the patient. In response to the comparison indicating any one of the cognitive state and the physical state prevent the caregiver from executing the tasks, an alert is generated. One or more recommendations for resolving the alert based on one or more recommendation rules are generated.

BRIEF DESCRIPTION OF THE SEVERAL VIEWS OF THE DRAWINGS

Referring now to the drawings in which like reference numbers represent corresponding parts throughout.

DETAILED DESCRIPTION

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Figure 1:
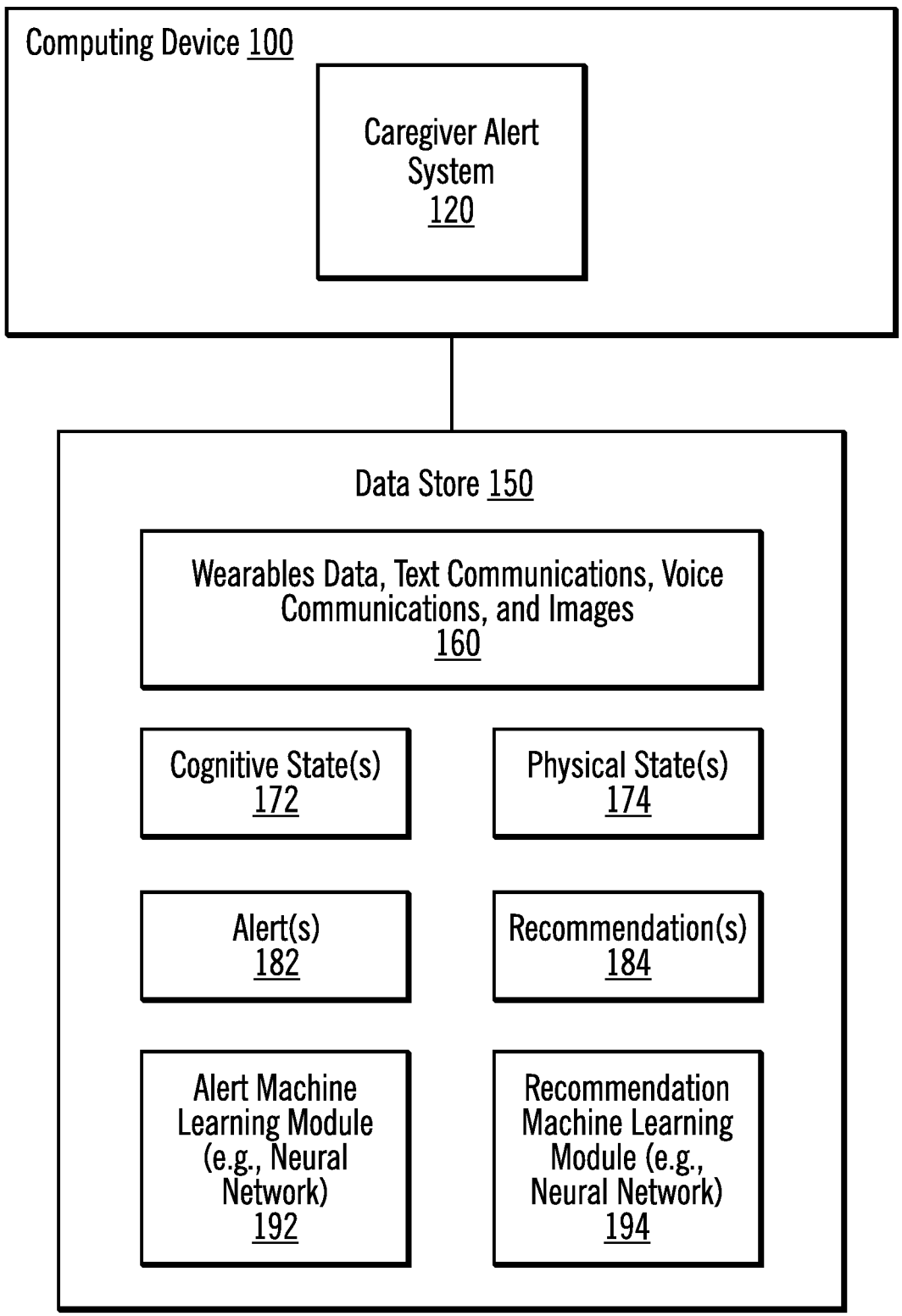
FIG. 1 illustrates, in a block diagram, a computing environment in accordance with certain embodiments.

FIG. 1 illustrates, in a block diagram, a computing environment in accordance with certain embodiments. A computer system 100 is coupled to a data store 150. The computer system 100 includes a caregiver alert system 120. The data store 150 stores wearables data, text communications, voice communications, and images 160 that provides data about the caregiver. The wearables data is obtained from sensors on wearable devices (e.g., smart watches or any other wearable devices that are capable of collecting a person's vital signs), and the wearables data includes, for example, blood pressure, pulse, temperature, breathing rate, oxygen level, etc. The text communications may be obtained from electronic mail messages ("emails"), text messages (e.g., instant messages), posts to websites (e.g., social networking sites). The voice communications may be obtained from listening to verbal conversations by the caregiver. From the text and voice communications, the caregiver alert system 120 may determine that the caregiver is talking about being tired or staying up late, etc. The images may be captured by the wearables or by other devices that have image capture capability, such as cameras (i.e., devices having cameras). From the images, the caregiver alert system 120 may determine facial expressions and whether the caregiver is slouching, yawning, etc.

The caregiver alert system 120 analyzes the wearables data, text communications, voice communications, and images 160 to generate one or more cognitive states 172 of a caregiver (e.g., emotion, sentiment level, etc. of the caregiver) and one or more physical states 174 of the caregiver (e.g., tired, focused, etc.). The emotion may indicate happy, sad, angry, etc., while the sentiment may indicate a positive or negative attitude. Then, the caregiver alert system 120 uses the one or more cognitive states 172 and the one or more physical states 174 to determine whether to issue one or more alerts 182 and one or more recommendations 184. In certain embodiments, an alert machine learning module 192 is used to generate the one or more alerts, while a recommendation machine learning module 194 is used to generate the one or more recommendations.

The caregiver alert system 120 provides alerts to indicate whether the caregiver is capable of taking care of a patient effectively while on a shift with a supportive circle of people who take care of the patient and who understand the needs of the caregiver.

Figure 2:
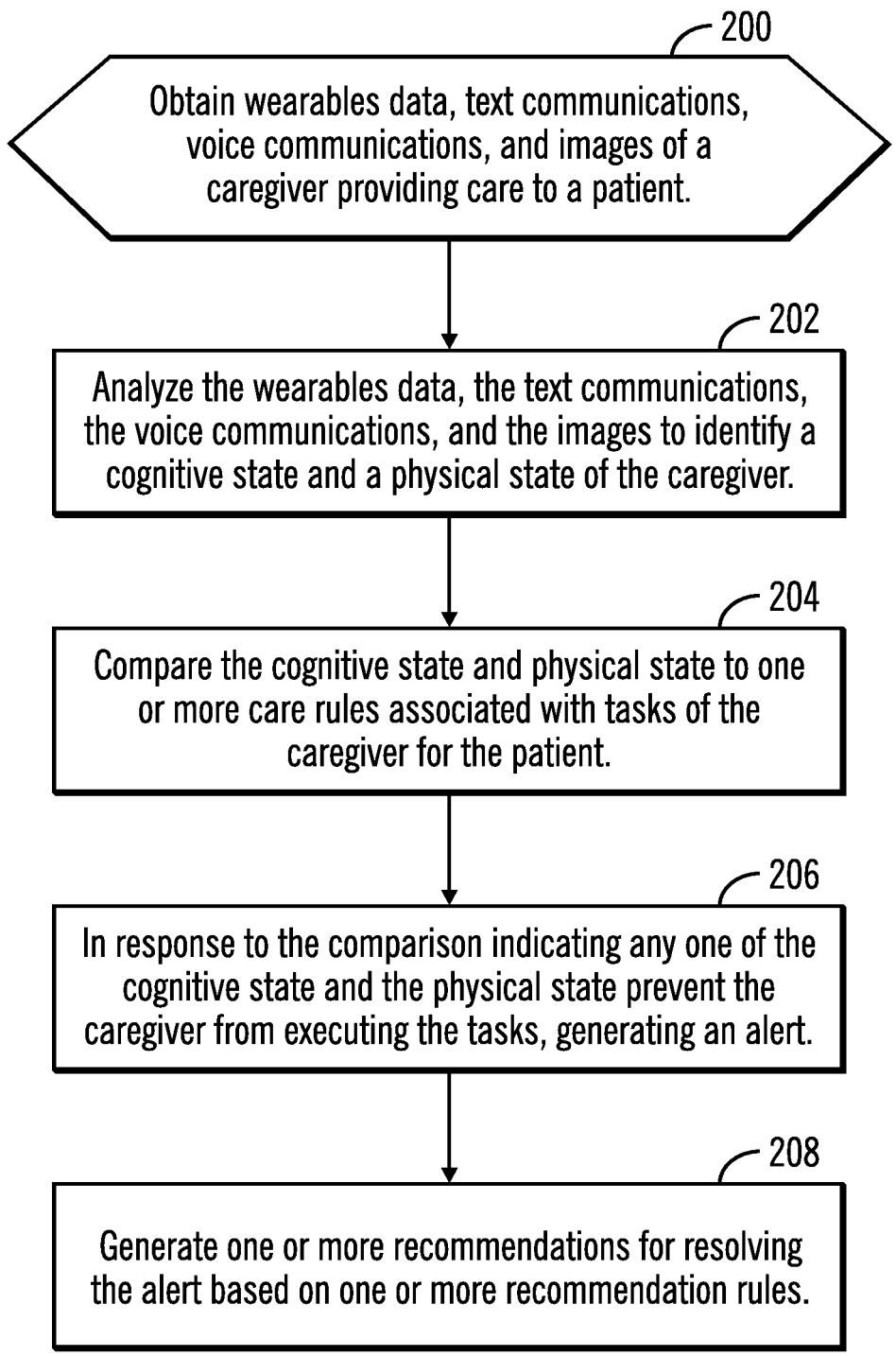
FIG. 2 illustrates, in a flowchart, operations for evaluating caregivers by monitoring care provided to a patient in accordance with certain embodiments.

FIG. 2 illustrates, in a flowchart, operations for evaluating caregivers by monitoring care provided to a patient in accordance with certain embodiments. Control begins at block 200 with the caregiver alert system 120 obtaining wearables data from wearable devices worn by the caregiver (e.g., a smart watch), text communications received and sent by the caregiver (e.g., by a smart phone), voice communications of a caregiver providing care to a patient (e.g., verbal communications), and images of the caregiver (e.g., from wearables data or from data of other devices with image capture capability). For example, the wearables data may indicate a rapid pulse and a high temperature. Continuing with the example, a text communication may indicate that the caregiver texted "I am tired". Also, a voice communication may indicate that the patient asked the caregiver "how are you?", and the caregiver indicated that caregiver could not sleep at night. In addition, an image (or series of images/video) may indicate that the caregiver is slouching.

In block 202, the caregiver alert system 120 analyzes the wearables data, the text communications, the voice communications, and the images to identify a cognitive state and a physical state of the caregiver. In certain embodiments, the voice communications are converted to text for analysis. In certain embodiments, the caregiver alert system 120 looks for key words in the text communications and the voice communications to determine the cognitive state and the physical state, and this may take into consideration how quickly the caregiver is speaking and how loudly the caregiver is speaking (relative to a stored recording of the caregiver when the caregiver is focused and not tired, etc.). In certain embodiments, the caregiver alert system 120 uses the text communications and the voice communications to determine whether the caregiver is speaking logically.

Continuing with the example, the caregiver alert system 120 may determine that the cognitive state is unfocused, while the physical state is slouching.

In block 204, the caregiver alert system 120 compares the cognitive state and the physical state to one or more care rules and thresholds associated with tasks of the caregiver for the patient. In doing this, the caregiver alert system 120 may determine a change in the level of care that the caregiver is providing based on the analysis of the wearable data, the texts, and the voice communications. In certain embodiments, the caregiver alert system 120 predefines a set of care rules and thresholds based on the tasks of the caregiver's job for the patient (which depends on the patient's condition). In certain embodiments, the caregiver alert system 120 performs image analysis of an image of the caregiver to detect whether the caregiver is shaking, yawning or slouching while taking care of the patient. Then, this may be compared to a rule that says: if the caregiver is unfocused in excess of a first threshold and is slouching in excess of a second threshold, issue an alert that the caregiver is not be able to take care of the patient. With this example, the threshold may indicate that if the unfocused state lasts longer than a first pre-determined amount of time and the slouching lasts longer than a second pre-determined period of time, then the alert is issued. For example, if the caregiver is unfocused and slouchy for more than 15 minutes, the alert may be issued.

The following is an example format of a care rule:

For task A—If [a cognitive state] exceeds [a first threshold] and/or [a physical state] exceeds [a second threshold], then issue [an alert]

In block 206, in response to the comparison indicating any one of the cognitive state and the physical state prevent the caregiver from executing the tasks, the caregiver alert system 120 generates an alert. For example, the alert may indicate that there has been a change in the level of care. The alert may be a noise, may be a text communication or email communication, etc. The caregiver alert system 120 may send the alert to the caregiver or an authorized user. For example, the authorized user may then intervene to replace the caregiver or help the caregiver. In certain embodiments, the authorized user represents a facility that provides caregivers for home care. In other embodiments, the authorized user is a friend or relative of the patient.

In block 208, the caregiver alert system 120 generates one or more recommendations for resolving the alert based on one or more recommendation rules. For example, a recommendation rule may indicate that if the alert is generated between 8:00 am and 8:00 pm, a first person is to be contacted to replace the caregiver, and, if the alert is generated after 8:00 pm, a second person is to be contacted to replace the caregiver. As another example, the caregiver alert system 120 may recommend that a caregiver who is physically closest to the patient (e.g., a shortest distance from the patient) be assigned to assist the patient. The caregiver alert system 120 monitors the caregiver's activities (after the caregiver has consented to such monitoring). The caregiver alert system 120 detects the caregiver's cognitive state and a physical state (i.e., the caregiver's conditions) through at least wearable devices, text communications posted to a social networking website and other personal communication tools (e.g., email and text messaging tools), voice communications through verbal conversations (e.g., face-to-face conversations or phone calls), and images (captured by wearables or other devices).

The following is an example format of a recommendation rule:

If [a cognitive state] is [a first state] and/or [a physical state] is a [second state] and/or [an alert] is [a particular alert], then issue [a specific recommendation]

In certain embodiments, the caregiver alert system 120 analyzes the caregiver's sentiment level to see whether the person is positive or negative. In certain embodiments, the caregiver alert system 120 analyzes the caregiver's current cognitive state to see whether the person's mind is focused, unfocused, alert, confused, etc. In certain embodiments, the caregiver alert system 120 analyzes the caregiver's current physical state to see whether the person is able to handle the tasks of a job (e.g., heavy lifting).

Examples will be provided here merely to enhance understanding. Embodiments are not intended to be limited to these examples.

For example, a caregiver taking care of a person with dementia performs a first set of tasks (e.g., cooking food and feeding the person), while a caregiver taking care of a person without dementia performs a second set of tasks (e.g., cooking food, but not feeding the person).

In certain embodiments, each of the tasks may be associated with a threshold having a value from a scale 1-10, and each care rule is associated with one of the tasks.

If a caregiver is taking care of a patient who has many demands, then there may be more tasks for the job than when taking care of a patient who is less demanding.

The caregiver alert system 120 compares the caregiver's current cognitive state and physical state with the tasks for the patient in the care rules.

If the caregiver alert system 120 detects that the caregiver's current cognitive state and physical state do not allow the caregiver to perform the tasks of the job, then the caregiver alert system 120 may perform any of: generating an alert and recommending alternative solutions.

Example recommendations include: changing to a different caregiver temporarily for the patient, having the caregiver take a break, recommending a different patient care plan (e.g., contacting the patient's family members to seek additional help if the facility that provided the caregiver does not have a replacement caregiver).

In one example use case, the caregiver alert system 120 monitors a caregiver's day-to-day activities. The caregiver alert system 120 expects the caregiver to be performing with full attention as she takes care of a patient with dementia. However, the caregiver was up through the night caring for a family member. The caregiver alert system 120 detects that the caregiver is yawning frequently and rubbing her eyes frequently during a shift. The caregiver alert system 120 determines that the caregiver is working a morning shift today and concludes that the caregiver had a difficult night and did not sleep much. The caregiver alert system 120 recommends that a new caregiver take over the shift for two hours so the tired caregiver is able to get some rest before returning to the shift.

Figure 3:
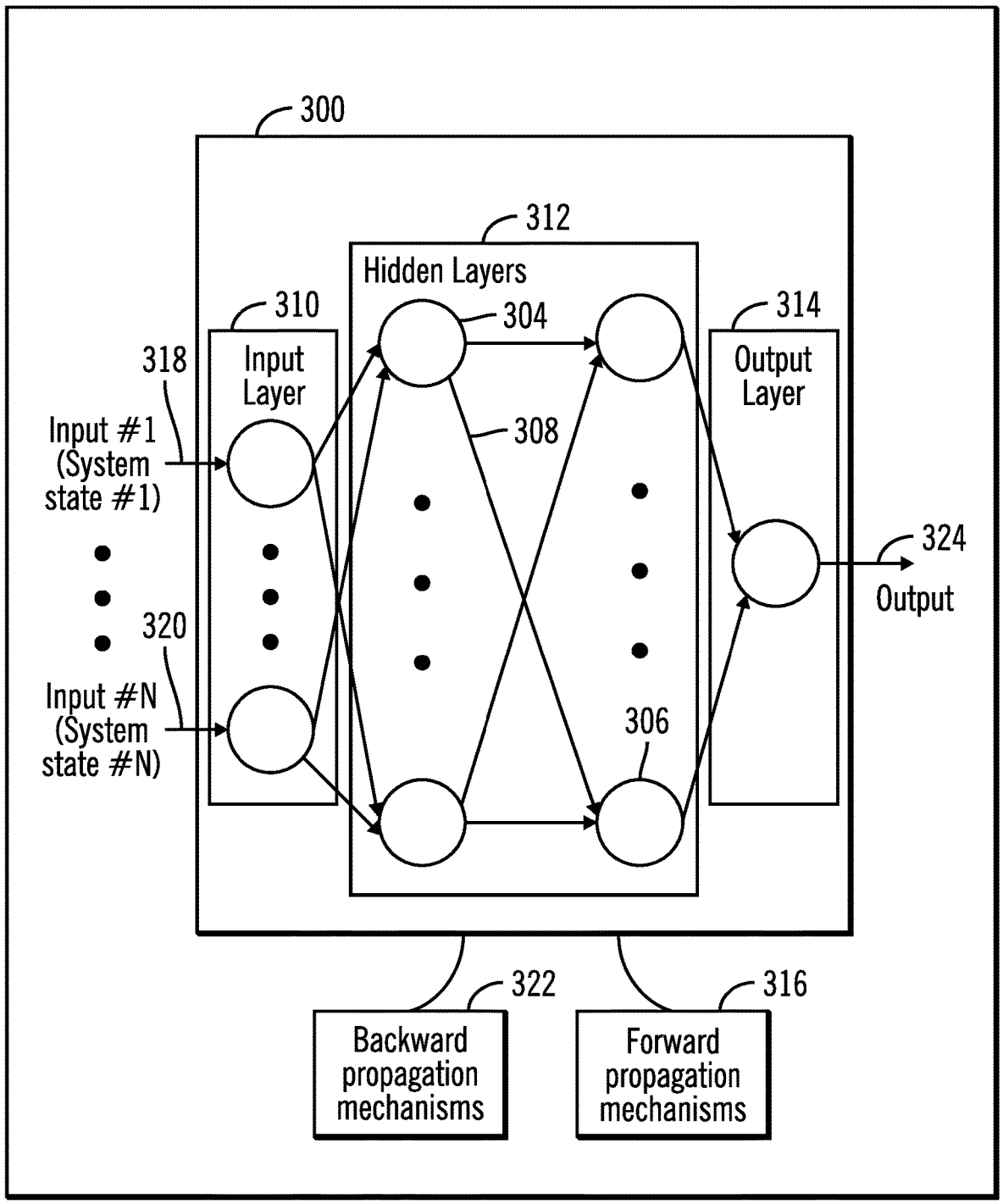
FIG. 3 illustrates, in a block diagram, details of a machine learning module in accordance with certain embodiments.

FIG. 3 illustrates, in a block diagram, details of a machine learning module 300 in accordance with certain embodiments. In certain embodiments, the alert machine learning module 192 and the recommendation machine learning module 194 are implemented using the components of the machine learning module 300.

The machine learning module 300 may comprise a neural network with a collection of nodes with links connecting them, where the links are referred to as connections. For example, FIG. 3 shows a node 304 connected by a connection 308 to the node 306. The collection of nodes may be organized into three main parts: an input layer 310, one or more hidden layers 312, and an output layer 314.

The connection between one node and another is represented by a number called a weight, where the weight may be either positive (if one node excites another) or negative (if one node suppresses or inhibits another). Training the machine learning module 300 entails calibrating the weights in the machine learning module 300 via mechanisms referred to as forward propagation 316 and backward propagation 322. Bias nodes that are not connected to any previous layer may also be maintained in the machine learning module 300. A bias may be described as an extra input of 1 with a weight attached to it for a node.

In certain embodiments, the input data 318 . . . 320 are examples of inputs 240, and output 324 is an example of output 324.

In forward propagation 316, a set of weights are applied to the input data 318 . . . 320 to calculate the output 324. For the first forward propagation, the set of weights may be selected randomly or set by, for example, a system administrator. That is, in the forward propagation 316, embodiments apply a set of weights to the input data 318 . . . 320 and calculate an output 324.

In backward propagation 322 a measurement is made for a margin of error of the output 324, and the weights are adjusted to decrease the error. Backward propagation 322 compares the output that the machine learning module 300 produces with the output that the machine learning module 300 was meant to produce, and uses the difference between them to modify the weights of the connections between the nodes of the machine learning module 300, starting from the output layer 314 through the hidden layers 312 to the input layer 310, i.e., going backward in the machine learning module 300. In time, backward propagation 322 causes the machine learning module 300 to learn, reducing the difference between actual and intended output to the point where the two come very close or coincide.

The machine learning module 300 may be trained using backward propagation to adjust weights at nodes in a hidden layer to produce adjusted output values based on the provided inputs 240. A margin of error may be determined with respect to the actual output 324 from the machine learning module 224 and an expected output to train the machine learning module 300 to produce the desired output value based on a calculated expected output. In backward propagation, the margin of error of the output may be measured and the weights at nodes in the hidden layers 312 may be adjusted accordingly to decrease the error.

Backward propagation may comprise a technique for supervised learning of artificial neural networks using gradient descent. Given an artificial neural network and an error function, the technique may calculate the gradient of the error function with respect to the artificial neural network's weights.

Thus, the machine learning module 300 is configured to repeat both forward and backward propagation until the weights of the machine learning module 300 are calibrated to accurately predict an output.

The machine learning module 300 implements a machine learning technique such as decision tree learning, association rule learning, artificial neural network, inductive programming logic, support vector machines, Bayesian models, etc., to determine the output value 324.

In certain machine learning module 300 implementations, weights in a hidden layer of nodes may be assigned to these inputs to indicate their predictive quality in relation to other of the inputs based on training to reach the output value 324 (e.g., alert or recommendation).

With embodiments, the machine learning module 300 is a neural network, which may be described as a collection of "neurons" with "synapses" connecting them.

With embodiments, there may be multiple hidden layers 312, with the term "deep" learning implying multiple hidden layers. Hidden layers 312 may be useful when the neural network has to make sense of something complicated, contextual, or non-obvious, such as image recognition. The term "deep" learning comes from having many hidden layers. These layers are known as "hidden", since they are not visible as a network output.

In certain embodiments, training a neural network may be described as calibrating all of the "weights" by repeating the forward propagation 316 and the backward propagation 322.

In backward propagation 322, embodiments measure the margin of error of the output and adjust the weights accordingly to decrease the error.

Neural networks repeat both forward and backward propagation until the weights are calibrated to accurately predict the output 324.

In certain embodiments, the inputs to the alert machine learning module 192 are the caregiver's cognitive state and physical state, and the outputs of the alert machine learning module 192 are one or more alerts. In certain embodiments, the inputs to the recommendation machine learning module 194 are any combination of the caregiver's cognitive state and physical state and the alerts, and the outputs of the recommendation machine learning module 194 are one or more recommendations. In certain embodiments, the machine learning model may be refined based on whether the outputted recommendations, once taken, generate positive outcomes.

Thus, embodiments determine the cognitive state and the physical state at runtime to determine whether the caregiver is qualified for the tasks to be performed in order to provide the best care for a patient.

With embodiments, the caregiver alert system 120 determines a current cognitive state (cognitive condition) and a current physical state (physical condition) of the caregiver based on receiving information from social media communications, voice communications, text communications, and one or more of sensors that are connected to one or more wearable devices. The caregiver alert system 120 determines whether the caregiver is able to perform tasks of a job based on comparing the current cognitive state and the current physical state with thresholds of care rules associated with the tasks of the job. In response to determining that the caregiver is not able to perform the tasks of the job, the caregiver alert system 120 provides one or more alerts and/or recommendations. With embodiments, different thresholds and different rules are associated with different tasks.

Figure 4:
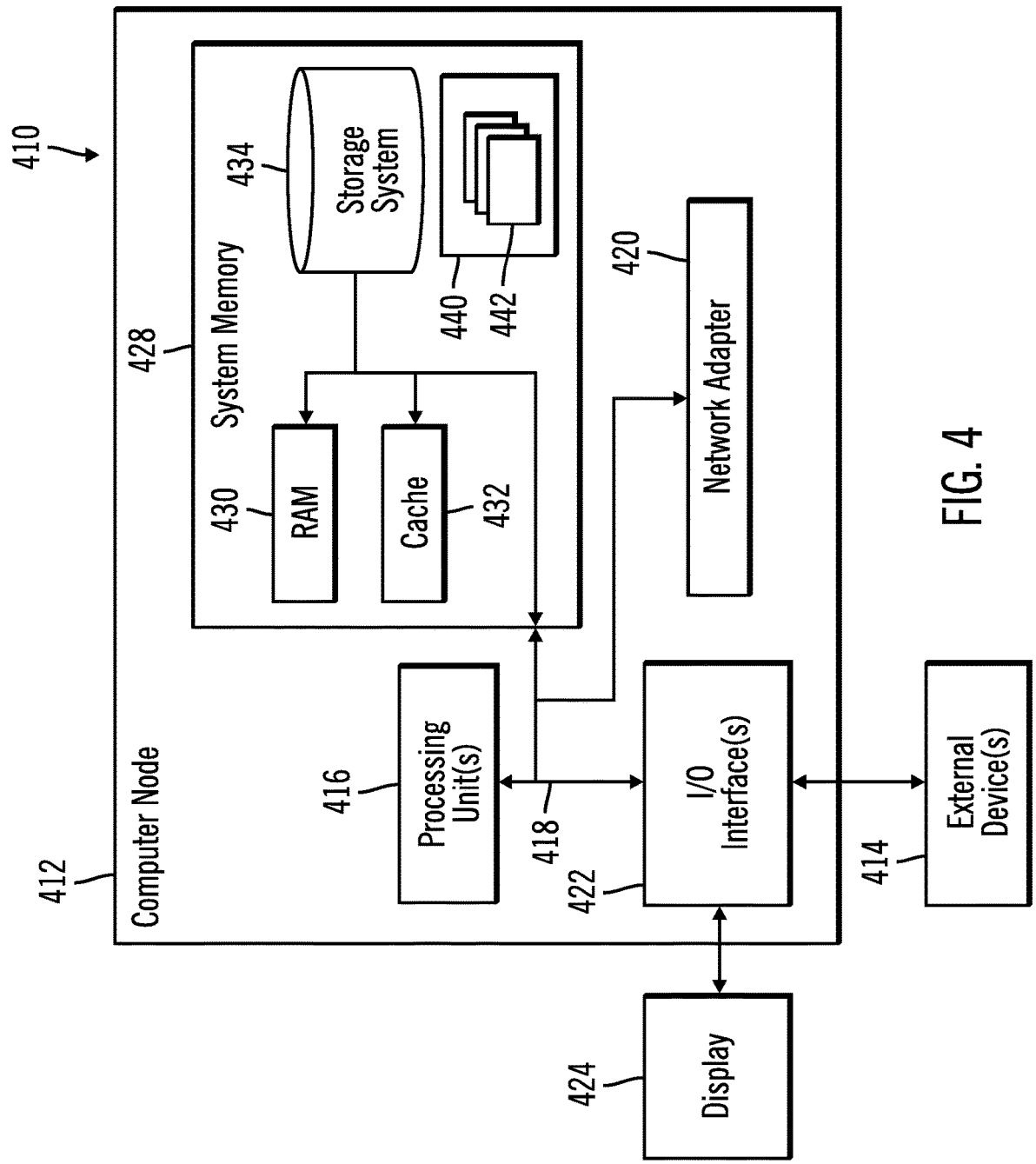
FIG. 4 illustrates a computing node in accordance with certain embodiments.

FIG. 4 illustrates a computing environment 410 in accordance with certain embodiments. In certain embodiments, the computing environment is a cloud computing environment. Referring to FIG. 4, computer node 412 is only one example of a suitable computing node and is not intended to suggest any limitation as to the scope of use or functionality of embodiments of the invention described herein. Regardless, computer node 412 is capable of being implemented and/or performing any of the functionality set forth hereinabove.

The computer node 412 may be a computer system, which is operational with numerous other general purpose or special purpose computing system environments or configurations. Examples of well-known computing systems, environments, and/or configurations that may be suitable for use with computer node 412 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer node 412 may be described in the general context of computer system executable instructions, such as program modules, being executed by a computer system. Generally, program modules may include routines, programs, objects, components, logic, data structures, and so on that perform particular tasks or implement particular abstract data types. Computer node 412 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer node 412 is shown in the form of a general-purpose computing device. The components of computer node 412 may include, but are not limited to, one or more processors or processing units 416, a system memory 428, and a bus 418 that couples various system components including system memory 428 to one or more processors or processing units 416.

Bus 418 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer node 412 typically includes a variety of computer system readable media. Such media may be any available media that is accessible by computer node 412, and it includes both volatile and non-volatile media, removable and non-removable media.

System memory 428 can include computer system readable media in the form of volatile memory, such as random access memory (RAM) 430 and/or cache memory 432. Computer node 412 may further include other removable/non-removable, volatile/non-volatile computer system storage media. By way of example only, storage system 434 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 418 by one or more data media interfaces. As will be further depicted and described below, system memory 428 may include at least one program product having a set (e.g., at least one) of program modules that are configured to carry out the functions of embodiments of the invention.

Program/utility 440, having a set (at least one) of program modules 442, may be stored in system memory 428 by way of example, and not limitation, as well as an operating system, one or more application programs, other program modules, and program data. Each of the operating system, one or more application programs, other program modules, and program data or some combination thereof, may include an implementation of a networking environment. Program modules 442 generally carry out the functions and/or methodologies of embodiments of the invention as described herein.

Computer node 412 may also communicate with one or more external devices 414 such as a keyboard, a pointing device, a display 424, etc.; one or more devices that enable a user to interact with computer node 412; and/or any devices (e.g., network card, modem, etc.) that enable computer node 412 to communicate with one or more other computing devices. Such communication can occur via Input/Output (I/O) interfaces 422. Still yet, computer node 412 can communicate with one or more networks such as a local area network (LAN), a general wide area network (WAN), and/or a public network (e.g., the Internet) via network adapter 420. As depicted, network adapter 420 communicates with the other components of computer node 412 via bus 418. It should be understood that although not shown, other hardware and/or software components could be used in conjunction with computer node 412. Examples, include, but are not limited to: microcode, device drivers, redundant processing units, external disk drive arrays, RAID systems, tape drives, and data archival storage systems, etc.

In certain embodiments, the computing device 100 has the architecture of computer node 412. In certain embodiments, the computing device 100 is part of a cloud infrastructure. In certain alternative embodiments, the computing device 100 is not part of a cloud infrastructure.

Cloud Embodiments

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
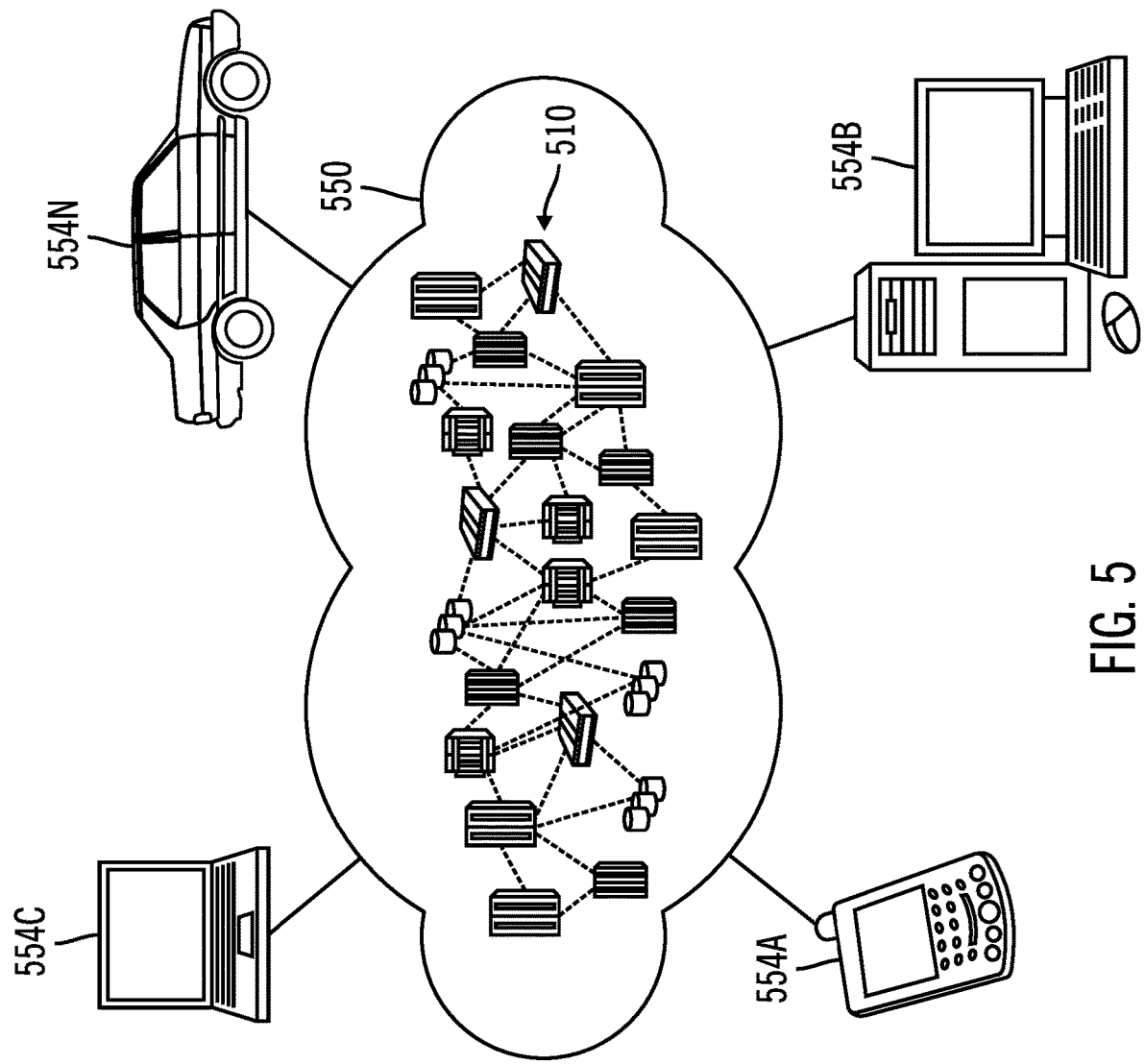
FIG. 5 illustrates a cloud computing environment in accordance with certain embodiments.

Referring now to FIG. 5, illustrative cloud computing environment 550 is depicted. As shown, cloud computing environment 550 includes one or more cloud computing nodes 510 with which local computing devices used by cloud consumers, such as, for example, personal digital assistant (PDA) or cellular telephone 554A, desktop computer 554B, laptop computer 554C, and/or automobile computer system 554N may communicate. Nodes 510 may communicate with one another. They may be grouped (not shown) physically or virtually, in one or more networks, such as Private, Community, Public, or Hybrid clouds as described hereinabove, or a combination thereof. This allows cloud computing environment 550 to offer infrastructure, platforms and/or software as services for which a cloud consumer does not need to maintain resources on a local computing device. It is understood that the types of computing devices 554A-N shown in FIG. 5 are intended to be illustrative only and that computing nodes 510 and cloud computing environment 550 can communicate with any type of computerized device over any type of network and/or network addressable connection (e.g., using a web browser).

Figure 6:
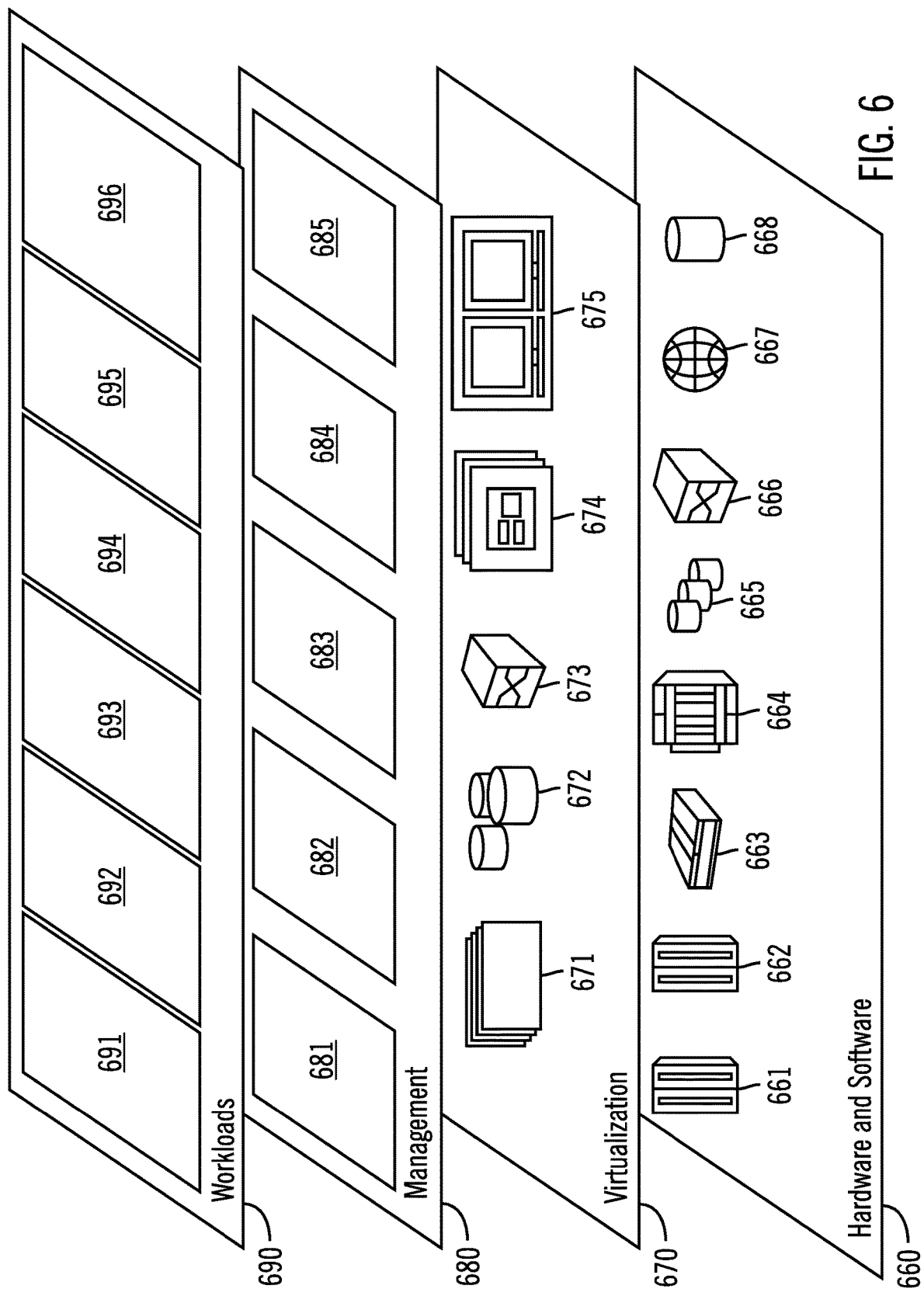
FIG. 6 illustrates abstraction model layers in accordance with certain embodiments.

Referring now to FIG. 6, a set of functional abstraction layers provided by cloud computing environment 550 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 660 includes hardware and software components. Examples of hardware components include: mainframes 661; RISC (Reduced Instruction Set Computer) architecture based servers 662; servers 663; blade servers 664; storage devices 665; and networks and networking components 666. In some embodiments, software components include network application server software 667 and database software 668.

Virtualization layer 670 provides an abstraction layer from which the following examples of virtual entities may be provided: virtual servers 671; virtual storage 672; virtual networks 673, including virtual private networks; virtual applications and operating systems 674; and virtual clients 675.

In one example, management layer 680 may provide the functions described below. Resource provisioning 681 provides dynamic procurement of computing resources and other resources that are utilized to perform tasks within the cloud computing environment. Metering and Pricing 682 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 683 provides access to the cloud computing environment for consumers and system administrators. Service level management 684 provides cloud computing resource allocation and management such that required service levels are met. Service Level Agreement (SLA) planning and fulfillment 685 provide pre-arrangement for, and procurement of, cloud computing resources for which a future requirement is anticipated in accordance with an SLA.

Workloads layer 690 provides examples of functionality for which the cloud computing environment may be utilized. Examples of workloads and functions which may be provided from this layer include: mapping and navigation 691; software development and lifecycle management 692; virtual classroom education delivery 693; data analytics processing 694; transaction processing 695; and alert generation based on a cognitive state and a physical state 696

Thus, in certain embodiments, software or a program, implementing alert generation based on a cognitive state and a physical state in accordance with embodiments described herein, is provided as a service in a cloud environment.

Additional Embodiment Details

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terms "an embodiment", "embodiment", "embodiments", "the embodiment", "the embodiments", "one or more embodiments", "some embodiments", and "one embodiment" mean "one or more (but not all) embodiments of the present invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the present invention need not include the device itself.

The foregoing description of various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing from the spirit and scope of the invention, embodiments of the invention reside in the claims herein after appended.

The foregoing description provides examples of embodiments of the invention, and variations and substitutions may be made in other embodiments.

What is claimed is:

1. A computer-implemented method, comprising operations for:
    obtaining wearables data, text communications, voice communications, and images of a caregiver providing care to a patient;
    analyzing the wearables data, the text communications, the voice communications, and the images to identify a cognitive state and a physical state of the caregiver;
    comparing the cognitive state and the physical state to one or more care rules associated with tasks of the caregiver for the patient;
    training an alerts machine learning module by calibrating first weights;
    in response to the comparison indicating any one of the cognitive state and the physical state prevent the caregiver from executing the tasks, generating an alert using the trained alerts machine learning module that receives inputs of the cognitive state and the physical state and outputs the alert;

training a recommendation machine learning module by calibrating second weights; and generating one or more recommendations for resolving the alert using the trained recommendation machine learning module that receives input of the cognitive state, the physical state, and the alert and outputs the one or more recommendations.

2. The computer-implemented method of claim 1, wherein the wearables data is obtained from sensors connected to one or more wearable devices, wherein the text communications are obtained from electronic mail messages, text messages, and posts to websites, wherein the voice communications are obtained from verbal conversations, and wherein the images are obtained from devices having cameras.

3. The computer-implemented method of claim 1, wherein the cognitive state indicates an emotion and a sentiment.

4. The computer-implemented method of claim 1, wherein each of the care rules includes a threshold.

5. The computer-implemented method of claim 1, wherein the one or more recommendations include a recommendation to change to another caregiver, a recommendation for the caregiver to take a break, and a recommendation to notify a contact of the patient.

6. The computer-implemented method of claim 1, wherein a Software as a Service (SaaS) is configured to perform the operations of the method.

7. A computer program product, the computer program product comprising a computer readable storage medium having program code embodied therewith, the program code executable by at least one processor to perform operations for:

obtaining wearables data, text communications, voice communications, and images of a caregiver providing care to a patient;

analyzing the wearables data, the text communications, the voice communications, and the images to identify a cognitive state and a physical state of the caregiver;

comparing the cognitive state and the physical state to one or more care rules associated with tasks of the caregiver for the patient;

training an alerts machine learning module by calibrating first weights;

in response to the comparison indicating any one of the cognitive state and the physical state prevent the caregiver from executing the tasks, generating an alert using the trained alerts machine learning module that receives inputs of the cognitive state and the physical state and outputs the alert;

training a recommendation machine learning module by calibrating second weights; and generating one or more recommendations for resolving the alert using the trained recommendation machine learning module that receives input of the cognitive state, the physical state, and the alert and outputs the one or more recommendations.

8. The computer program product of claim 7, wherein the wearables data is obtained from sensors connected to one or more wearable devices, wherein the text communications are obtained from electronic mail messages, text messages, and posts to websites, wherein the voice communications are obtained from verbal conversations, and wherein the images are obtained from devices having cameras.

9. The computer program product of claim 7, wherein the cognitive state indicates an emotion and a sentiment.

10. The computer program product of claim 7, wherein each of the care rules includes a threshold.

11. The computer program product of claim 7, wherein the one or more recommendations include a recommendation to change to another caregiver, a recommendation for the caregiver to take a break, and a recommendation to notify a contact of the patient.

12. The computer program product of claim 7, wherein a Software as a Service (SaaS) is configured to perform the operations of the computer program product.

13. A computer system, comprising:

one or more processors, one or more computer-readable memories and one or more computer-readable, tangible storage devices; and program instructions, stored on at least one of the one or more computer-readable, tangible storage devices for execution by at least one of the one or more processors via at least one of the one or more computer-readable memories, to perform operations comprising:

obtaining wearables data, text communications, voice communications, and images of a caregiver providing care to a patient;

analyzing the wearables data, the text communications, the voice communications, and the images to identify a cognitive state and a physical state of the caregiver;

comparing the cognitive state and the physical state to one or more care rules associated with tasks of the caregiver for the patient;

training an alerts machine learning module by calibrating first weights;

in response to the comparison indicating any one of the cognitive state and the physical state prevent the caregiver from executing the tasks, generating an alert using the trained alerts machine learning module that receives inputs of the cognitive state and the physical state and outputs the alert;

training a recommendation machine learning module by calibrating second weights; and generating one or more recommendations for resolving the alert using the trained recommendation machine learning module that receives input of the cognitive state, the physical state, and the alert and outputs the one or more recommendations.

14. The computer system of claim 13, wherein the wearables data is obtained from sensors connected to one or more wearable devices, wherein the text communications are obtained from electronic mail messages, text messages, and posts to websites, wherein the voice communications are obtained from verbal conversations, and wherein the images are obtained from devices having cameras.

15. The computer system of claim 13, wherein the cognitive state indicates an emotion and a sentiment.

16. The computer system of claim 13, wherein each of the care rules includes a threshold.

17. The computer system of claim 13, wherein a Software as a Service (SaaS) is configured to perform the operations of the computer system.

18. The computer system of claim 13, wherein the one or more recommendations include a recommendation to change to another caregiver, a recommendation for the caregiver to take a break, and a recommendation to notify a contact of the patient.

* * * * *